United States Patent [19]

Bilstad et al.

[11] Patent Number: 4,479,762

[45] Date of Patent: Oct. 30, 1984

[54] PREPACKAGED FLUID PROCESSING MODULE HAVING PUMP AND VALVE ELEMENTS OPERABLE IN RESPONSE TO APPLIED PRESSURES

[75] Inventors: Arnold C. Bilstad, Deerfield; Richard I. Brown, Northbrook; Robert J. Kruger, Arlington Heights, all of Ill.

[73] Assignee: Baxter Travenol Laboratories, Inc., Deerfield, Ill.

[21] Appl. No.: 453,926

[22] Filed: Dec. 28, 1982

[51] Int. Cl.³ ............................................. A61M 1/03
[52] U.S. Cl. .................................. 417/395; 206/364; 206/570
[58] Field of Search ............... 417/394, 395, 479, 480, 417/510; 128/DIG. 3, DIG. 12; 604/4, 5, 6, 152, 153, 246; 206/570, 571, 572, 364, 365, 366

[56] References Cited

U.S. PATENT DOCUMENTS

| | | |
|---|---|---|
| Re. 27,849 | 12/1973 | Wortman . |
| D. 271,801 | 12/1983 | Preussner . |
| D. 271,802 | 12/1983 | Preussner . |
| 2,308,974 | 1/1943 | Harper ................................ 417/510 |
| 2,356,738 | 8/1944 | Brugger ......................... 417/510 X |
| 2,980,032 | 4/1961 | Schneider ...................... 417/395 X |
| 3,007,416 | 11/1961 | Childs ............................. 417/479 X |
| 3,148,624 | 9/1964 | Baldwin ......................... 417/479 X |
| 3,154,021 | 10/1964 | Vick ................................... 417/394 |
| 3,250,224 | 5/1966 | Phillips et al. . |
| 3,298,320 | 1/1967 | Latham ........................... 417/479 X |
| 3,518,033 | 6/1970 | Anderson ............................ 417/478 |
| 3,656,873 | 4/1972 | Schiff ................................. 417/395 |
| 3,689,204 | 9/1972 | Prisk .................................. 417/394 |
| 3,709,222 | 1/1973 | DeVries ......................... 417/395 X |
| 3,741,687 | 6/1973 | Nystroem ...................... 417/395 X |
| 3,771,174 | 11/1973 | Wortman . |
| 3,774,762 | 11/1973 | Lichtenstein ................ 210/321.3 X |
| 3,912,455 | 10/1975 | Lichtenstein .................. 128/765 X |
| 3,946,731 | 3/1976 | Lichtenstein ................. 128/DIG. 3 |
| 4,042,153 | 8/1977 | Callahan et al. ............... 417/478 X |
| 4,047,844 | 9/1977 | Robinson ....................... 417/395 X |
| 4,121,236 | 10/1978 | Welp et al. . |
| 4,158,530 | 6/1979 | Bernstein ....................... 417/394 X |
| 4,160,505 | 7/1979 | Rauschenberger ................ 206/571 |
| 4,199,307 | 4/1980 | Jassawalla ..................... 417/479 X |
| 4,211,597 | 7/1980 | Lipps et al. . |
| 4,236,880 | 12/1980 | Archibald ...................... 417/479 X |
| 4,250,872 | 2/1981 | Tamari ........................... 417/394 X |
| 4,273,121 | 6/1981 | Jassawalla ..................... 417/479 X |
| 4,276,004 | 6/1981 | Hahn .............................. 417/540 X |
| 4,277,226 | 7/1981 | Archibald ........................... 417/38 |
| 4,290,346 | 9/1981 | Bujan ................................. 417/478 |
| 4,303,376 | 12/1981 | Siekmann ...................... 417/395 X |
| 4,364,716 | 12/1982 | Schjeldahl ......................... 417/394 |
| 4,379,452 | 4/1983 | DeVries ................................ 604/6 |
| 4,411,866 | 10/1983 | Kanno . |
| 4,412,553 | 11/1983 | Kopp et al. . |

FOREIGN PATENT DOCUMENTS

| | | |
|---|---|---|
| 982874 | 2/1976 | Canada................................ 417/395 |
| 2723197 | 8/1977 | Fed. Rep. of Germany . |
| 2093800 | 10/1983 | United Kingdom . |

OTHER PUBLICATIONS

Jeanette Scott, "Membrane and Ultrafiltration Technology", (1980).

Primary Examiner—Leonard E. Smith
Attorney, Agent, or Firm—Paul C. Flattery; Daniel D. Ryan; Eugene M. Cummings

[57] ABSTRACT

A disposable prepackaged fluid processing module includes an integral housing wherein fluid containers, tubing segments, and other components required in processing a fluid are contained. Fluid communication between the containers, components and tubing segments is provided by a fluid circuit formed by a panel of the housing, and an overlying fluid-impermeable flexible sheet member. The fluid circuit includes pump and valve elements which operate in response to pressures applied to the sheet member. Upon installation of the system in a related actuator apparatus pneumatic actuator ports apply pressures to the pump and valve elements to circulate fluid through the fluid circuit.

46 Claims, 32 Drawing Figures

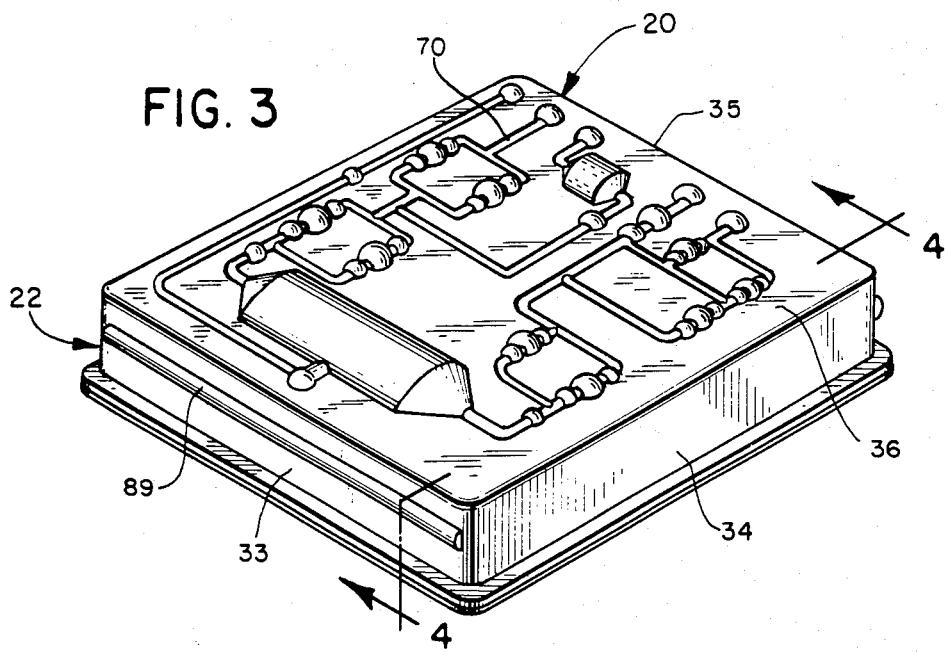
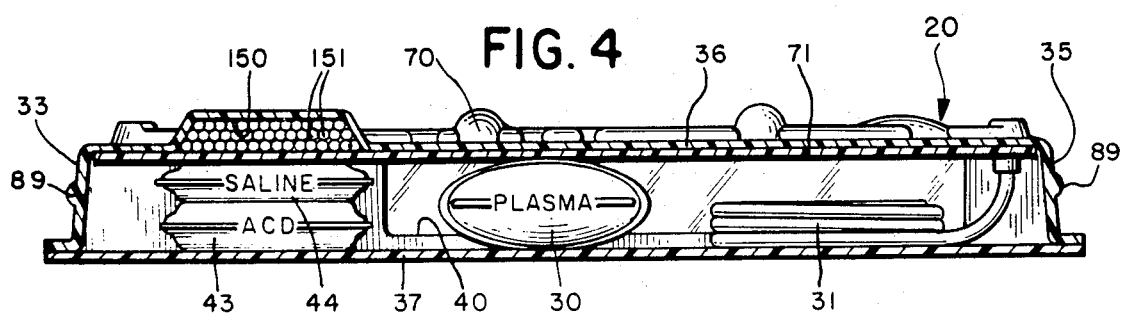

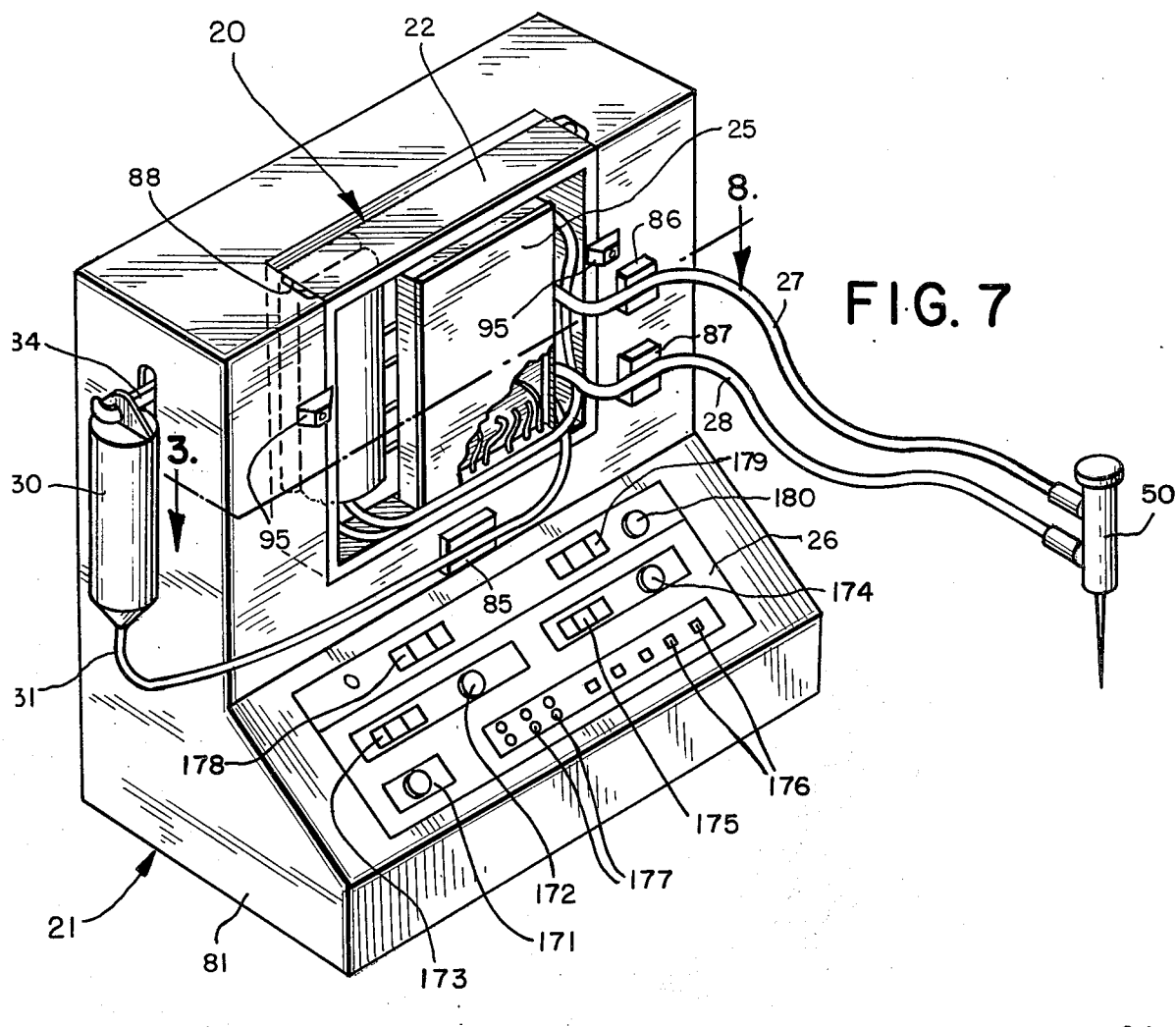

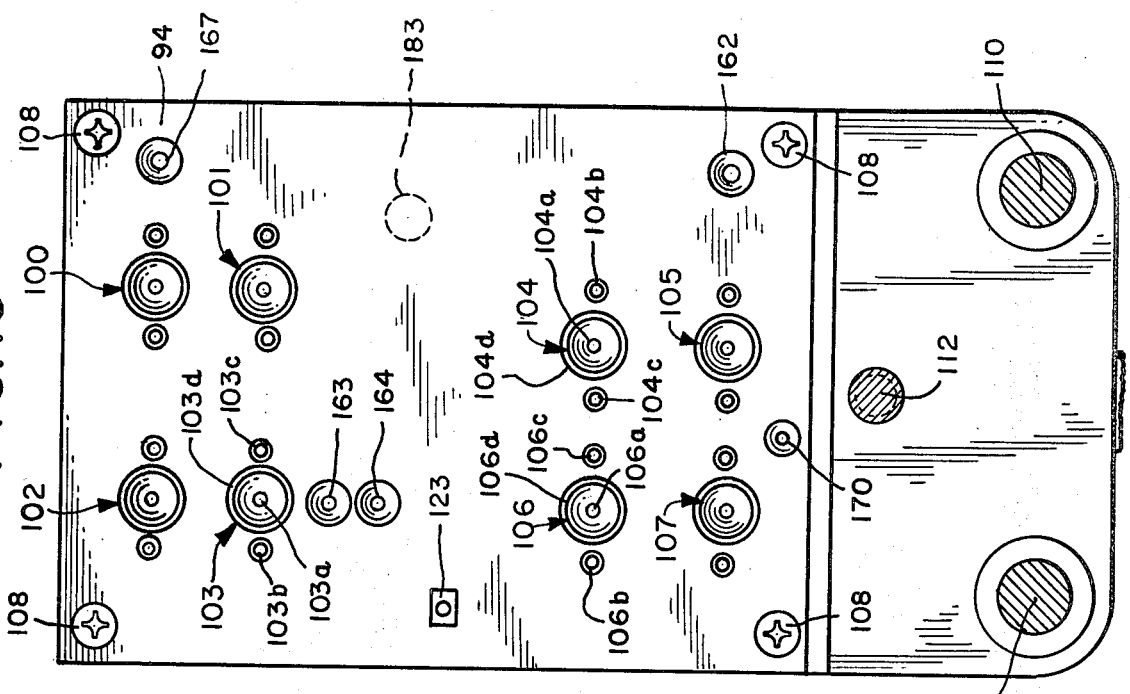
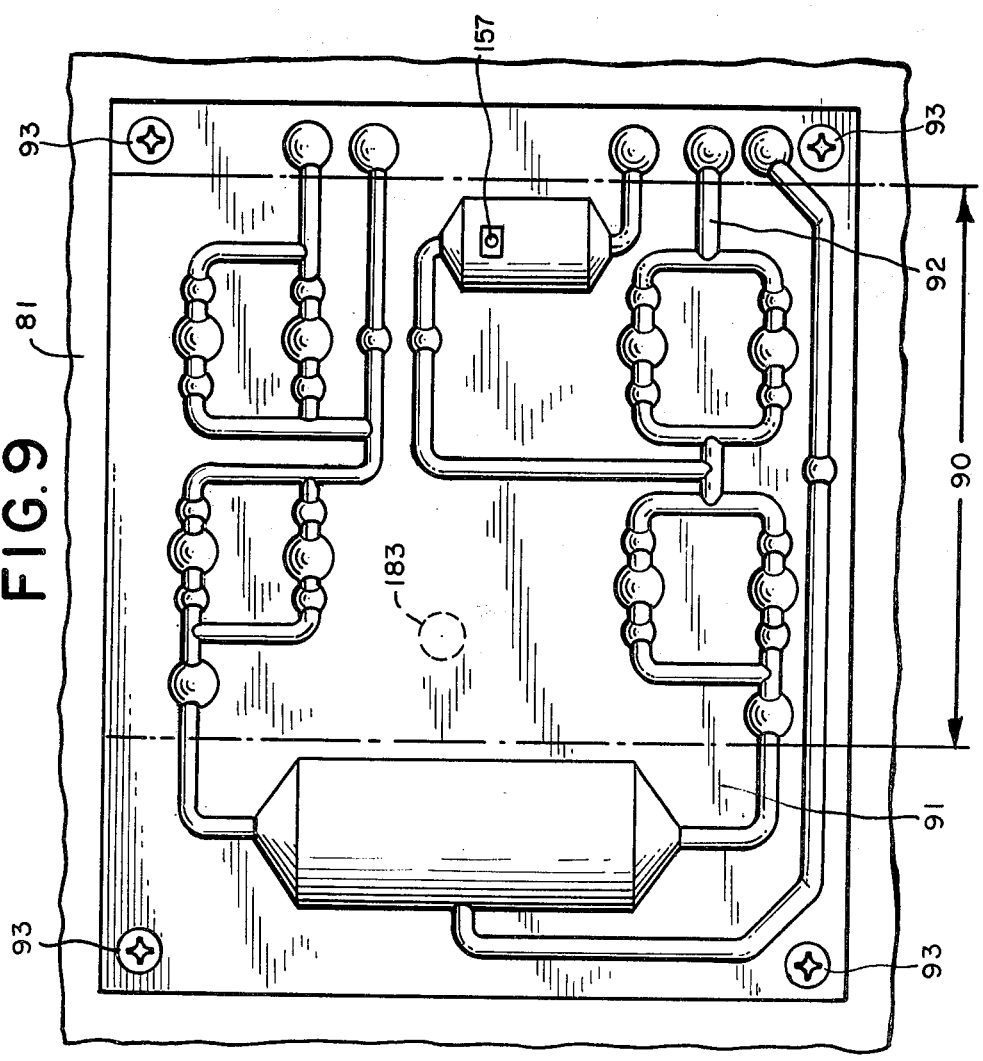

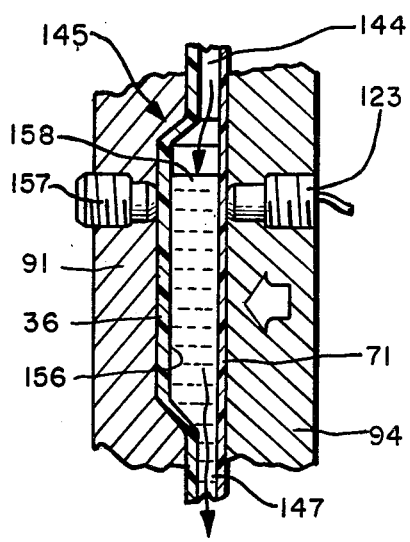
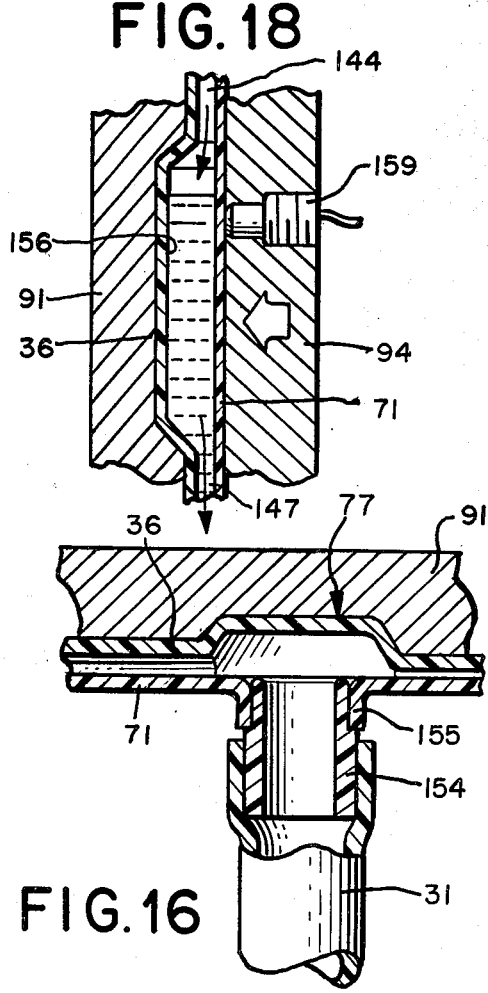
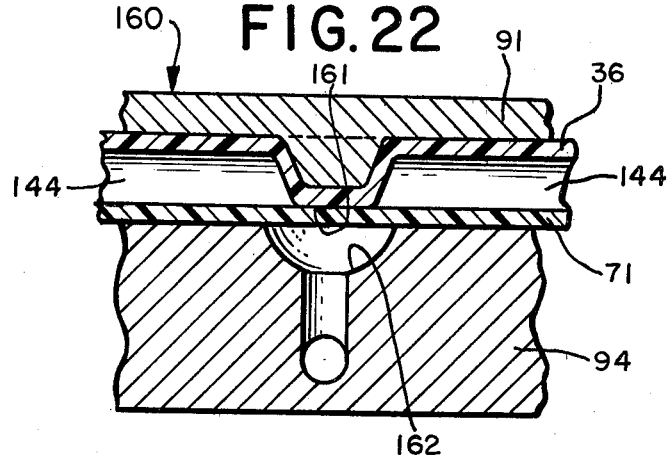
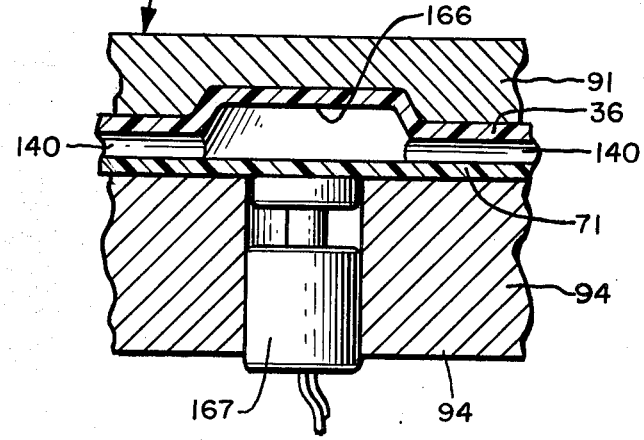
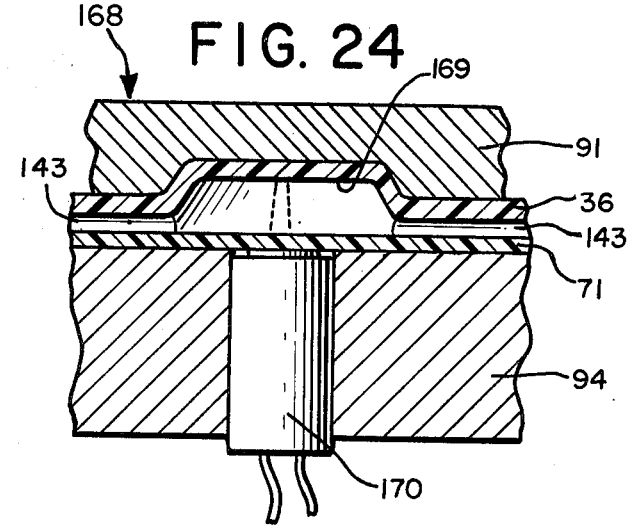

AT REST

FILL STROKE

PUMP STROKE

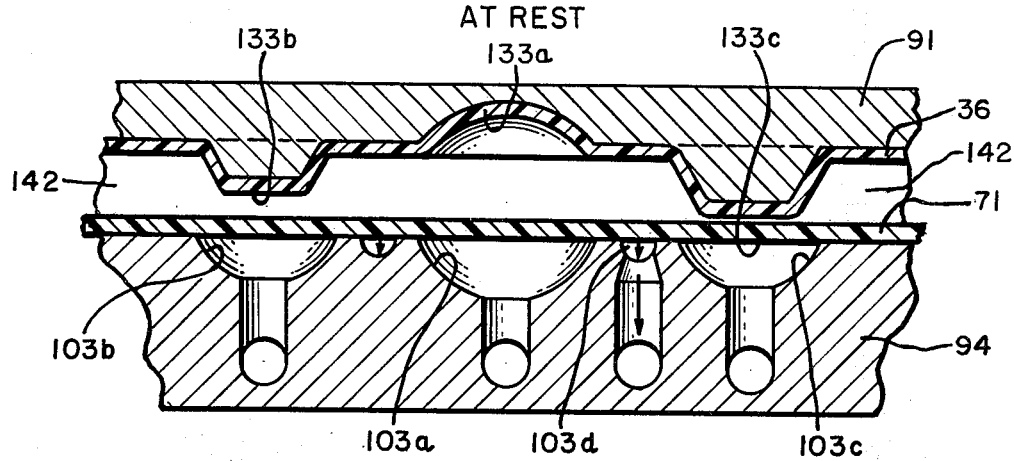
FIG. 20A AT REST
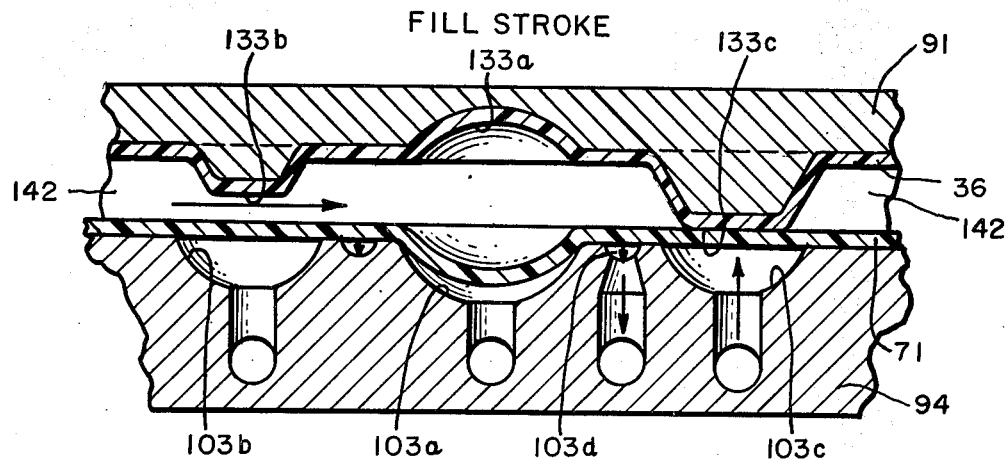
FIG. 20B FILL STROKE
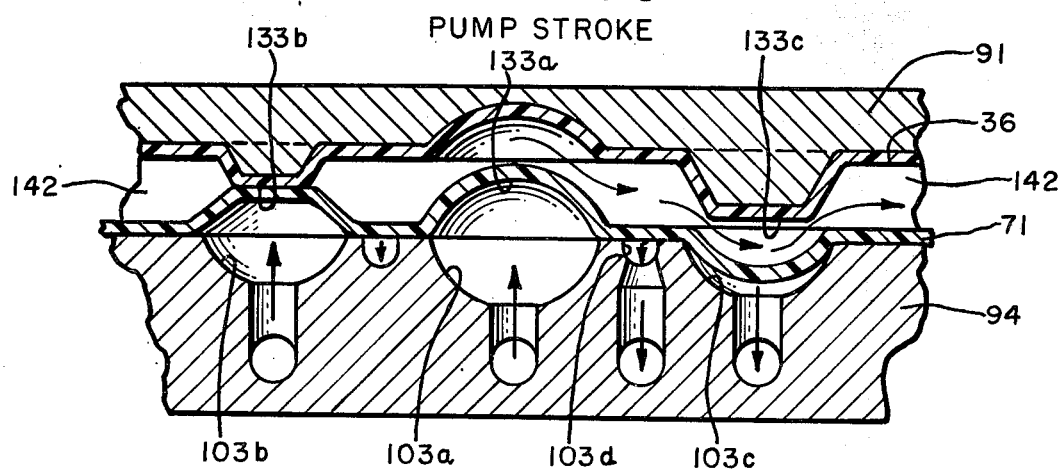
FIG. 20C PUMP STROKE

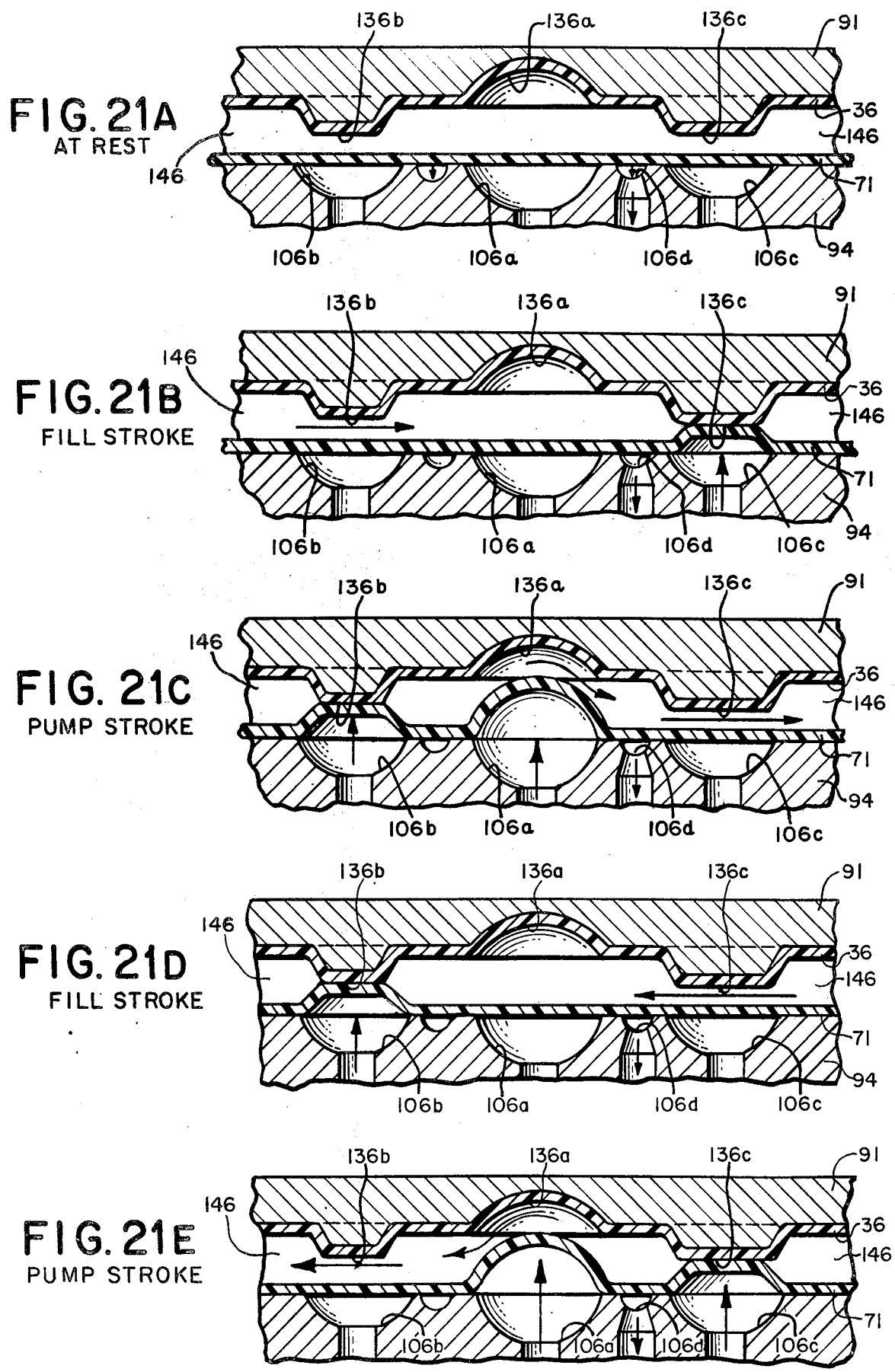

PREPACKAGED FLUID PROCESSING MODULE HAVING PUMP AND VALVE ELEMENTS OPERABLE IN RESPONSE TO APPLIED PRESSURES

BACKGROUND OF THE INVENTION

The present invention relates generally to fluid processing systems, and more specifically to a self-contained prepackaged fluid processing module which can be conveniently stored, set-up and operated.

Various methods and apparatus have been developed which utilize disposable single-use processing systems formed of plastics such as vinyl for accomplishing fluid processing procedures. In the medical field, for example, processing systems have been developed for blood fractionation procedures, such as plasmapheresis, leukopheresis and plateletpheresis, wherein whole blood is separated into one or more fractions by means of either a filter element or by means of centrifugation, and for hemodialysis procedures, wherein diffusion exchange occurs through a membrane between whole blood and a dialysis solution.

In these, and in other medical procedures employing disposable fluid processing systems, it is typically necessary for an attendant to first select and locate an appropriate filter or membrane element and one or more flow sets. The packaging of these items must then be opened and the items must be connected together to form a fluid circuit, which is then installed on the particular processor apparatus with which the procedure is to be performed.

Typically, the processor apparatus includes multiple pump, detector and clamping elements on which particular components and tubing segments of the fluid circuit must be individually installed. Consequently, the set-up procedure may be undesirably complex so as to require a specially trained operator, and may require an undesirably long time period to complete. Furthermore, even with the use of a specially trained technician, the potential remains for error, as where the wrong tubing segment is installed on a particular element of the apparatus.

Accordingly, the need has developed in the medical field for a modular fluid processing system which contains in a single storable package all of the components required for a particular procedure, and wherein the connections between system components are clearly identified and pre-established so that the system can be quickly set-up and installed on an associated processor apparatus. Preferably, such a system and the associated apparatus should be constructed so as to avoid the need for installing individual tubing segments and components of the system on individual pump, monitor and clamp elements of the apparatus. Furthermore, such a fluid processing system should contain all fluid containers necessary for fluids dispensed and collected in the procedure, so that the operator need only install the system in the actuator apparatus and connect input and output tubing segments to the donor prior to beginning a procedure.

Previous attempts at reducing the complexity of fluid processing systems for medical procedures have centered on arranging a portion of the fluid circuit in a block or manifold so as to interface with a complementarily configured actuator station on a processor apparatus. Typically, such systems did not provide containers for storing fluids, such as saline or ACD, and components required in the procedures. Consequently, it was necessary for the operator to separately assemble these component and make the necessary connections, with attendant delays and potential for error.

The present invention is directed to a prepackaged fluid processing module which satisfies the above requirements in a form which is economical to produce and convenient to store. The system is particularly advantageous in medical procedures where a relatively complex fluid circuit is required in conjunction with a multiple pump, sensing and control elements.

The invention is particularly useful in continuous-flow blood fractionation procedures, such as plasmapheresis, wherein plasma (or other blood component) is removed by means of a hollow-fiber filter, and wherein a relatively complex and exacting valving and pumping regimen is required to control blood flow to and from the patient. Accordingly, the invention is illustrated herein in conjunction with a blood fractionation circuit, although it will be appreciated that the invention can be configured to provide other fluid circuits for other medical and non-medical procedures.

Accordingly, it is a general object of the present invention to provide a new and improved disposable fluid processing system.

It is a further object of the present invention to provide a fluid processing system which is modular in construction and wherein the components and interconnections required therein are contained within a single disposable housing.

It is a further object of the present invention to provide a disposable fluid processing module which includes an integral housing for storing the principal components thereof, and wherein a panel of the housing forms, in conjunction with an overlying fluid impermeable plastic sheet member, a low-volume fluid circuit for interconnecting the various components and tubing segments of the system.

It is a further object of the present invention to provide a fluid processing system which is modular for storage, and which can be readily configured for installation on an associated fluid processor apparatus.

It is a further object of the present invention to provide a modular fluid processing system wherein fluid flow is controlled to minimize damage to cellular material processed therein.

SUMMARY OF THE INVENTION

The invention is directed to a disposable fluid circuit which comprises a relatively rigid fluid-impermeable panel member including an outwardly depressed portion thereon. A fluid-impermeable flexible sheet member overlies the panel member to form in conjunction with the depressed portions a fluid-sealed fluid circuit. The invention is further directed to a fluid module for performing a fluid processing procedure having a housing including a base panel and a side panel, the base panel comprising an element of a fluid circuit as described above, wherein a component required in the procedure is contained within the housing.

The invention is further directed to a fluid processing circuit, as described above, wherein the fluid circuit includes pump elements actuable by externally applied forces to establish a controlled flow of fluid through the fluid circuit.

The invention is further directed to a fluid processing circuit, as described above, wherein the fluid circuit includes fluid absence, pressure or hemolysis detectors formed in conjunction with the housing panel and the flexible sheet member.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 3 is a perspective view of the bottom of the modular fluid processing system showing the fluid circuit formed on the bottom panel thereof.

FIG. 4 is a cross-sectional view of the modular processing module taken along line 4—4 of FIG. 1.

FIG. 7 is a perspective view of the processing module showing the system installed in the actuator station of the processor apparatus of FIG. 6.

FIG. 8 is a cross-sectional view of the processing module and the actuator station of the processor apparatus taken along line 8—8 of FIG. 7.

FIG. 9 is a front elevational view of the back plate provided in the actuator station for engaging the rear surface of the housing of the processing module.

FIG. 10 is a front elevational view of the movable actuator head assembly provided in the actuator station of the processor apparatus.

FIG. 16 is a cross-sectional view of a connector fitting of the fluid circuit taken along line 16—16 of FIG. 13.

FIG. 17 is a cross-sectional view of the fluid absence detector incorporated in the fluid circuit taken along line 17—17 of FIG. 13.

FIG. 18 is a cross-sectional view similar to FIG. 17 showing an alternative construction for a fluid absence detector.

FIGS. 20A–20C are enlarged cross-sectional views of a normally-open pump element of the fluid circuit showing the element in at rest, fill and pump conditions, respectively.

FIGS. 21A–21E are enlarged cross-sectional views of a bidirectional pump element of the fluid circuit showing the element in at rest, fill and pump conditions in one direction, and in fill and pump conditions in the other direction, respectively.

FIG. 22 is a cross-sectional view of a pressure regulator element of the fluid circuit taken along line 22—22 of FIG. 13.

FIG. 23 is a cross-sectional view of a pressure sensor element of the fluid circuit taken along line 23—23 of FIG. 13.

FIG. 24 is a cross-sectional view of a hemolysis detector element of the fluid circuit taken along line 24—24 of FIG. 13.

DESCRIPTION OF THE PREFERRED EMBODIMENT

Figure 1:
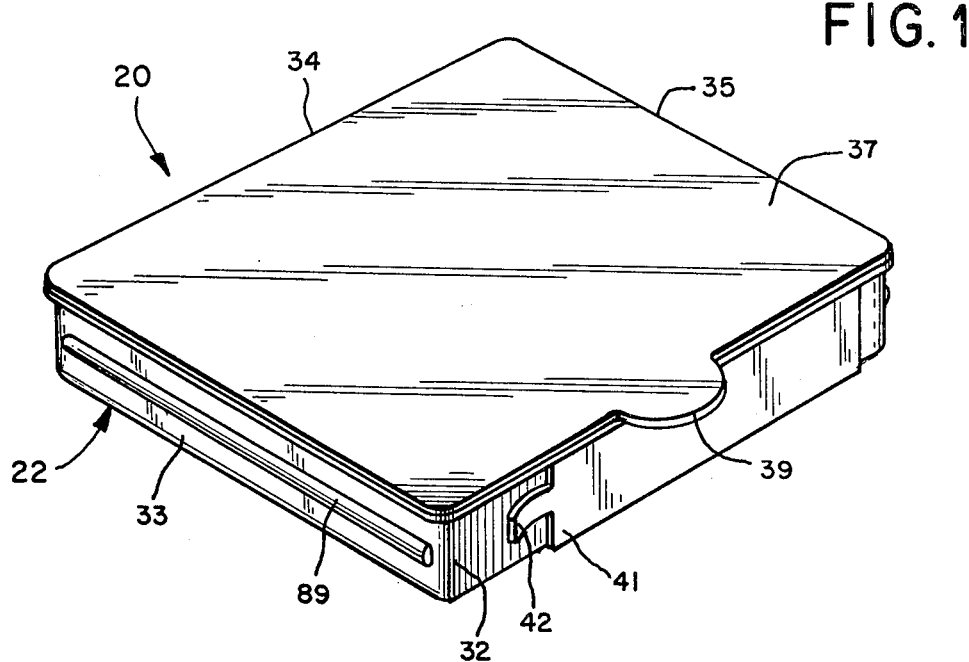
FIG. 1 is a perspective view of a modular fluid processing system constructed in accordance with the invention for continuous-flow plasmapheresis, showing the cover thereof in place and the system configured for long term storage.

Referring to the drawings, and particularly to FIGS. 1–7, a prepackaged fluid processing module 20 is shown constructed in accordance with the invention for performing a fluid processing procedure in conjunction with an associated actuator apparatus 21. The module 20 includes a compact, normally closed housing 22 in which the fluid circuit and all the associated components required in the procedure are carried in a prearranged and, preferably, preattached condition. The housing 22 thus serves, in part, as a compact storage container to protect the fluid circuit and components prior to use.

Figure 6:
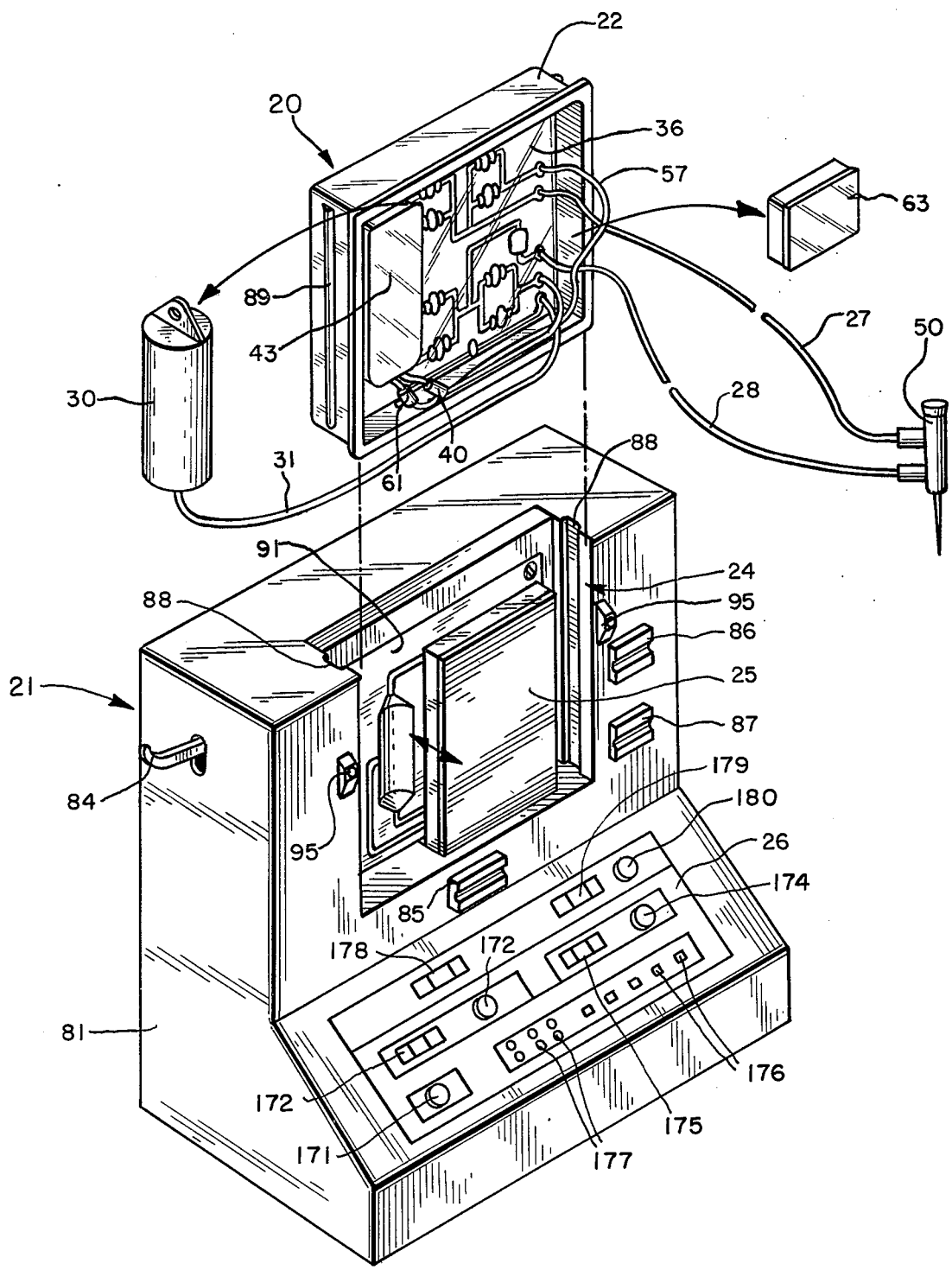
FIG. 6 is a perspective view of the processing module, disassembled and positioned for installation in the actuator station of an associated processor apparatus providing a continuous flow separation of plasma from whole blood.

At the time of use, as shown in FIGS. 6 and 7, the housing by reason of its unique construction, can be opened and conveniently placed in operative association with an actuator station 24 of the actuator apparatus 21, which provides pumping and valving actions necessary in the fluid circuit of the module for accomplishing the desired procedure. To this end, the actuator station may include an actuator head assembly 25 for engaging the housing, and a control panel 26 by which operating parameters for the procedure may be set by the operator.

The prepackaged, easily handled module 20, along with the associated actuator apparatus 21, are suited for use with virtually any fluid system. As will soon become apparent, the module 20 significantly simplifies the handling of fluid circuits, both prior to and during use, and all but eliminates the possibilities of an incorrectly arranged flow system or an incorrectly connected pump.

These inherent advantages of the modular flow system of the invention particularly lend the invention to use in fluid processing systems in the medical field, and particularly for fractionating or otherwise processing blood. For this reason, use of the module 20 in this context will be described.

While the specific blood processing procedure performed by the module 20 may vary, in the illustrated embodiment a fluid circuit for performing a continuous flow membrane plasmapheresis procedure is shown. During this plasmapheresis procedure, whole blood is drawn from a donor through a tubing segment 27 and separated into a plasma component and a red blood cell component. The red blood cell component is returned to the donor through a tubing segment 28. The plasma component is delivered to a container 30 through a tubing segment 31 for fractionation into various therapeutic components, such as albumin or Clotting Factor VIII.

Figure 2:
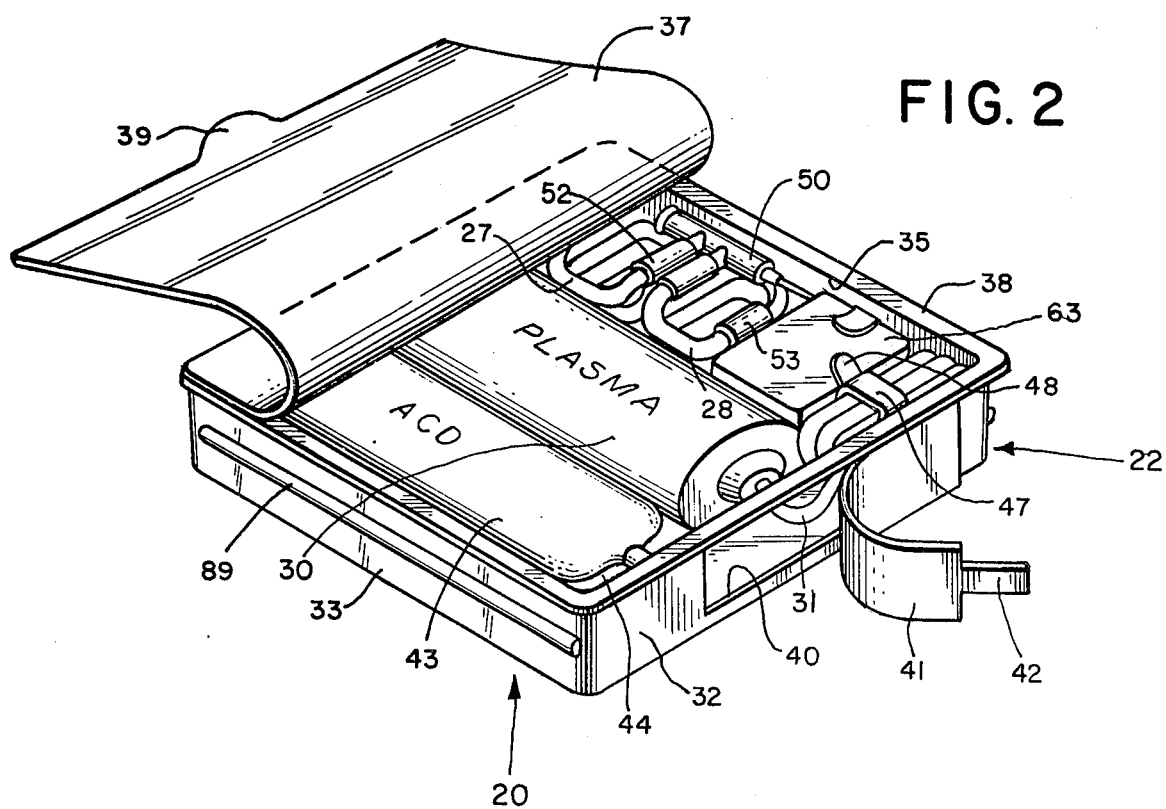
FIG. 2 is a perspective view of the modular processing system with the cover substantially removed to show the placement of the principal components of the system therein.

Referring now to FIGS. 1-5, the housing 22 is seen to comprise four side panels 32-35 and a bottom panel 36 formed of a relatively rigid, fluid-impervious material, preferably translucent, clear or colored, and not opaque to light, such as molded plastic. The housing 22 is normally closed and sealed for long term storage by means of a cover 37, which is sealed over the open end of the housing. The cover may be formed of a flexible, fluid-impervious material such as metallic foil or vinyl, and may be secured by means of a layer 38 of adhesive or other appropriate means to the edge of the housing, as shown in FIG. 2. The housing side panels 32-35 preferably include an outwardly projecting rim portion to facilitate this attachment. A pull tab 39 may be provided to assist the operator in removing the cover at time of use.

To facilitate the desired operative interface between the module 20 and the actuator station 24 of processor apparatus 21, an elongated aperture 40 (see, in particular, FIG. 2) is provided in side panel 32. This aperture 40 is normally closed and sealed during storage by means of a cover 41, which extends over the aperture and is secured to side panel 32 by a layer of adhesive or other appropriate means. A pull tab 42 may be provided to facilitate removal of cover 41 from side panel 32 when preparing the processing system for use.

In accordance with one aspect of the invention, the fluid circuit and all the components required to perform the particular desired procedure can be conveniently carried within the confines of the housing 22. In the context of a continuous flow plasmapheresis procedure, containers are required for storing an anticoagulant solution (such as ACD or CPDA), a saline solution, and the collected plasma. Accordingly, the fluid processing system located within the housing in the illustrated embodiment includes a prefilled ACD container 43, a prefilled saline container 44 and the empty plasma collection container 30.

The prefilled ACD container 43 and saline container 44 are preferably formed of flexible vinyl material. To prevent the contents of the containers 43 and 44 from evaporating through the vinyl walls of the containers, a suitable over-wrap (not shown) is preferably provided to form a vapor barrier around the containers.

The containers 43 and 44 may be stored within housing 22 in an unconnected condition with the associated fluid circuit. In this arrangement, at the time of use, containers 43 and 44 are removed from the housing 22, the overwraps are removed, and the containers are then connected by the operator in flow communication with the circuit. In making the connection in an open or aseptic system, a conventional blood "spike" carried on tubing connected to the fluid circuit can be used to pierce a membrane associated with the inlet port of the end container. Alternately, in making the connection in a closed or sterile system, a sterile connector device can be used to interconnect the containers 43 and 44 with the fluid system, such as disclosed in Granzow, U.S. Pat. No. 4,157,723.

Preferably, the containers 43 and 44 are stored within the housing in a preattached condition with the fluid circuit. The containers 43 and 44, along with the associated overwraps may be integrally connected with the circuit using a port block, such as disclosed in Boggs et al, U.S. patent application Ser. No. 282,894, filed July 13, 1981 and entitled "Port Block Assembly For Interconnecting a Fluid Container with a Fluid Conduit". In this arrangement, the containers 43 and 44 are preferably permanently secured within housing 22 by adhesive attachment to the interior surface of the adjacent side panel 34.

When in a preattached condition, the ACD container 43 is integrally connected to the fluid circuit of the processing system by a tubing segment 56, which includes a frangible in-line cannula 57 (see FIG. 5), such as disclosed in Bayham et al, U.S. Pat. No. 4,294,247. This cannula 57 is preferably arranged so as to be readily accessible to the operator upon removing cover 37, and preferably also includes a pull tab 58 containing indicia and/or color coding to draw the operator's attention to the cannula 57 during the set-up procedure.

Similarly, when preattached, the saline container 44 is integrally connected to the fluid circuit by means of a tubing segment 60 which includes another frangible in-line cannula 61. This cannula 61 is also preferably positioned for ready access to the operator upon removing cover 27, and also includes a pull tab 62 containing indicia and/or color coding to assist the operator in locating and fracturing the cannula during set-up.

Figure 5:
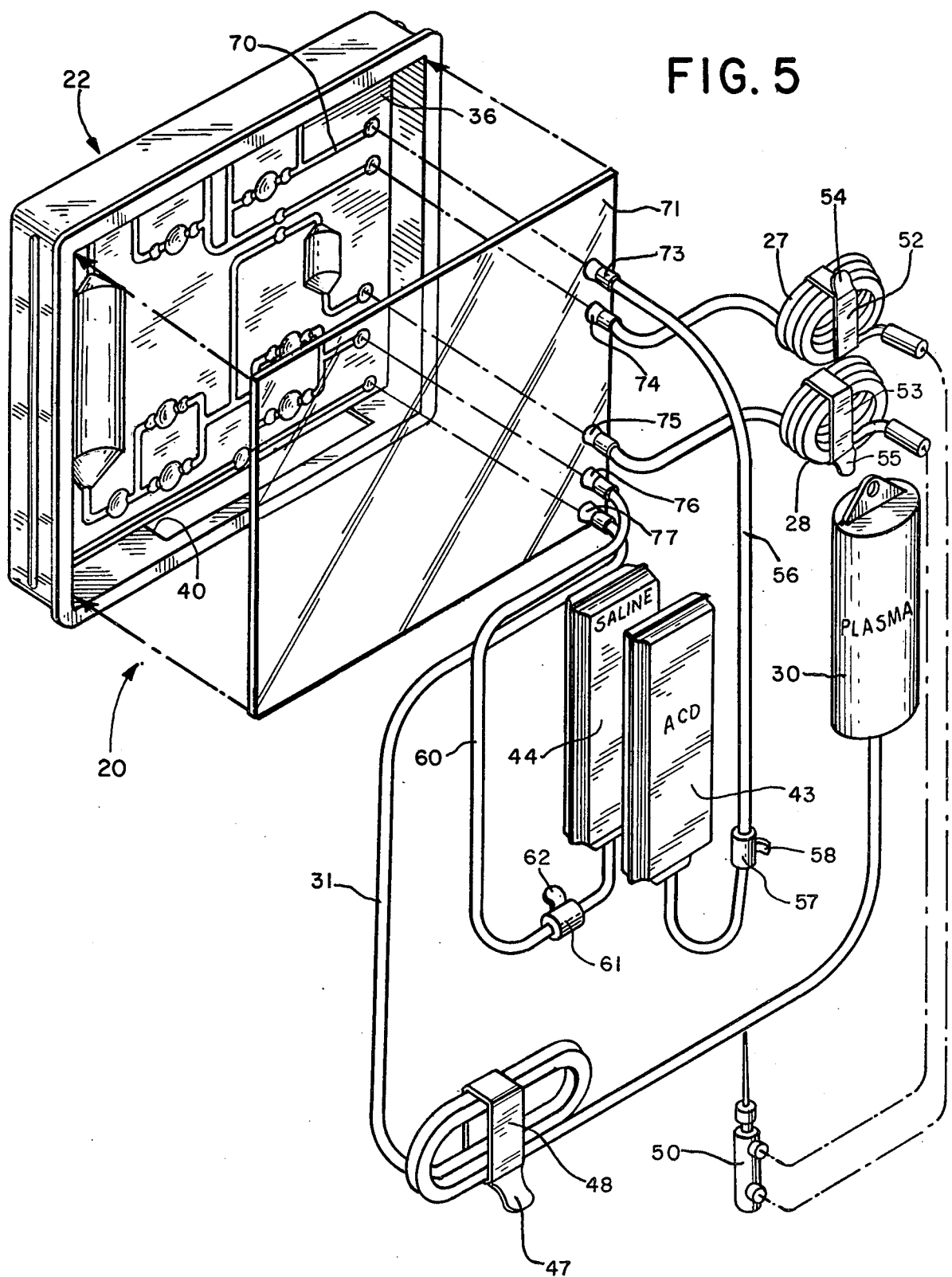
FIG. 5 is an exploded perspective view of the processing module showing the principal components and interconnections thereof.

Plasma container 30, which may be in the form of an unbreakable bottle of the type which conforms to standards established for long term plasma storage, is preferably not permanently secured and can be removed by the system operator at time of use. As is best shown in FIG. 5, tubing segment 31 is preferably prearranged in a compact bundle in housing 22 and secured by an adhesive strip 47 or other appropriate means to an adjacent side panel 32 (see FIG. 2) so as to be readily accessible when preparing the processing system for use. A pull tab 48 bearing appropriate indicia and/or color coding may be provided at one end of adhesive strip 47 to facilitate removing the strip from the tubing bundle.

Tubing segments 27 and 28 are each connected at one end to the processing circuit, and at their other end to respective ports of a conventional dual lumen phlebotomy needle 50 to accommodate a "single needle" plasmapheresis procedure. Alternately, each tubing segment 27 and 28 could individually communicate with a separate phlebotomy needle to accommodate a "two needle" plasmapheresis procedure.

Tubing segments 27 and 28 are also each preferably prearranged in a compact coil within housing 22 and secured by respective adhesive strips 52 and 53 in this form. Pull tabs 54 and 55 identified by appropriate indicia and/or color coding may be provided to assist the operator in locating and removing the adhesive strips from these tubing segment coils.

As shown in FIG. 4, the ACD and saline containers 43 and 44 can be generally wide and relatively flat so as to accommodate their compact stacking one-above-the-other within the housing 22. The plasma container 30, which, as previously described, is preferably in the form of a standard plasma collection bottle, can then be conveniently positioned to one side of the stacked saline and ACD containers 43 and 44 so as to allow room for tubing coils 27, 28, and 31.

Additional ancillary components and items required during the plasmapheresis process may be contained within a small rectangular miscellaneous supplies container 63, disposed within housing 22 (see FIG. 2). This container 63 may include hypodermic needles, bandages, surgical tape, antiseptic solution, and other items incidental to the procedure.

As shown in FIGS. 3 and 4, the bottom panel 36 of the housing 22 is molded or vacuum formed to include portions 70 which project or bow outwardly from the housing interior. Together, these portions 70 define in the interior surface of the bottom panel the fluid flow pattern required to perform the plasmapheresis procedure. This preformed fluid circuit also includes a plurality of chambers which provide necessary valving, pumping, filtering and fluid detection capabilities when the system is installed in actuator station 24.

As is best shown in FIG. 5, the preformed fluid circuit defined in the interior portion of bottom panel 36 is sealed by means of a fluid-impermeable flexible plastic sheet member 71 which fits over the interior surface of the bottom panel 36. This flexible sheet member 71 is preferably dimensioned to correspond to the inside peripheral dimensions of bottom panel 36 and is secured over the panel 56 by RF welding, or other appropriate means. Together, the portions 70 and the overlying flexible sheet member 71 form the entire fluid-sealed fluid circuit within the module.

Fluid communication is selectively established with the fluid circuit by means of five connector fittings 73–77 which extend through respective apertures in flexible sheet member 71. When sheet 71 is sealed in position against the inside surface of bottom panel 36, the connector fittings align and engage respective ones of five inlet/outlet port locations preformed on the interior surface of the back panel 36. Tubing segment 56 is connected to connector 73 at one end and to the ACD container 43 at its other end. Tubing segment 27 is connected at one end to connector 73 and at its other end to the needle 50. Tubing segment 28 is connected to connector 74 at one end and to the needle 50 at its other end. Tubing segment 60 is connected between connector 76 and saline container 44. Tubing segment 31 is connected between connector 77 and plasma collection container 30. Fluid flow into and out of the fluid circuit is thus provided.

By virtue of this above-described construction, each of the components contained within housing 22 is interconnected in a preattached condition for storage and eventual use in a plasmapheresis procedure. No additional interconnections need be made by the operator during set-up Referring to FIG. 6, prior to use of the processing module 20, the cover 37 is removed and the plasma collection container 30, tubing segments 27, 28 and 31, and the accessories container 63 are removed from housing 22. The cover 41 is then removed, and the module system is installed in the actuator station 24 of processor apparatus 21, which provides the fluid pumping, valving and monitoring functions necessary in accomplishing the plasmapheresis procedure. Significantly, and in accordance with another aspect of the invention, all of these functions are accomplished without the necessity of individually installing tubing segments and other components of the system in separate pumping, valving and sensing elements of the apparatus. Instead, upon installation of the module 20 in the actuator station 24 of the processor apparatus, all such functions are realized automatically without individual attention by the operator and without interrupting the integrity of the fluid circuit of the processing system.

In accordance with the invention, fluid pumping and valving functions are achieved by application of pressure forces to the flexible sheet member 71 which overlies the bottom panel 36 of housing 22. To this end, actuator apparatus 21, which is described in the copending application of the present inventors, entitled "Actuator Apparatus for a Prepackaged Fluid Processing Module Having Pump and Valve Elements Operable In Response to Applied Pressures" Ser. No. 453,920, filed concurrently herewith, includes a housing 81 having a generally vertical portion within which the actuator station 24 is provided for receiving housing 22, and a lower base portion on which control panel 26 is provided. A hanger arm 84 is provided on the left (as viewed in FIG. 6) side of the upper housing portion to support the plasma collection container 30, and three tubing retention blocks 85–87 are provided for supporting respective ones of tubing segments 31, 27 and 28 when housing 22 is seated in station 24.

Actuator station 24, which is dimensioned to receive housing 22 in sliding engagement, may include a pair of slots 88 for engaging ribs 89 molded into the side of the housing to maintain the housing in accurate alignment. In operation, pressure communication with the processing system is established by means of the movable actuator head 25 within actuator station 24. When housing 22 is installed in station 24, the actuator head extends through aperture 40 in side panel 32 so as to overlie a portion 90 (FIGS. 9 and 13) of sheet member 71 and the underlying portion of bottom panel 36. To enable pressure forces to be applied to the flexible sheet member 71, the actuator head is brought into engagement with the sheet member by reciprocative movement toward the rear of actuator station 24. This causes the bottom panel and sheet member to be compressed between the head and a back plate 91 at the rear of the station.

As shown in FIG. 9, the back plate 91 may include a series of depressions, collectively identified as 92, arranged to receive the raised portions 70 of bottom panel 36. The back plate 91 may be secured to the housing 81 of processor 21 by means of a plurality of machine screws 93, or other appropriate fastening means. By removing back plate 91 and substituting a different back plate having a different pattern of depressions 92, apparatus 21 can be reconfigured for other fluid processing procedures. A pair of retaining clamps 95 may be provided for holding the module 20 in actuator station 24.

As shown in FIGS. 8–12, the actuator head assembly 25 includes an actuator plate 94 which is brought into engagement with sheet member 71. As shown in FIG. 10, this actuator plate includes eight pneumatic pump actuator elements 100–107 which apply a vacuum and/or pressure control effect to appropriate portions of sheet member 71 associated with corresponding pump elements in the fluid circuit defined by the sheet member and bottom panel 36 to obtain necessary pumping and valving functions. The actuator plate 94 is preferably mounted within actuator head assembly 25 by means of a plurality of machine screws 108, or other appropriate fastening means, so that the actuator plate can be removed and a different actuator plate having a different arrangement of vacuum actuator ports can be substituted when reconfiguring the processor apparatus for a different fluid processing procedure.

Figure 11:
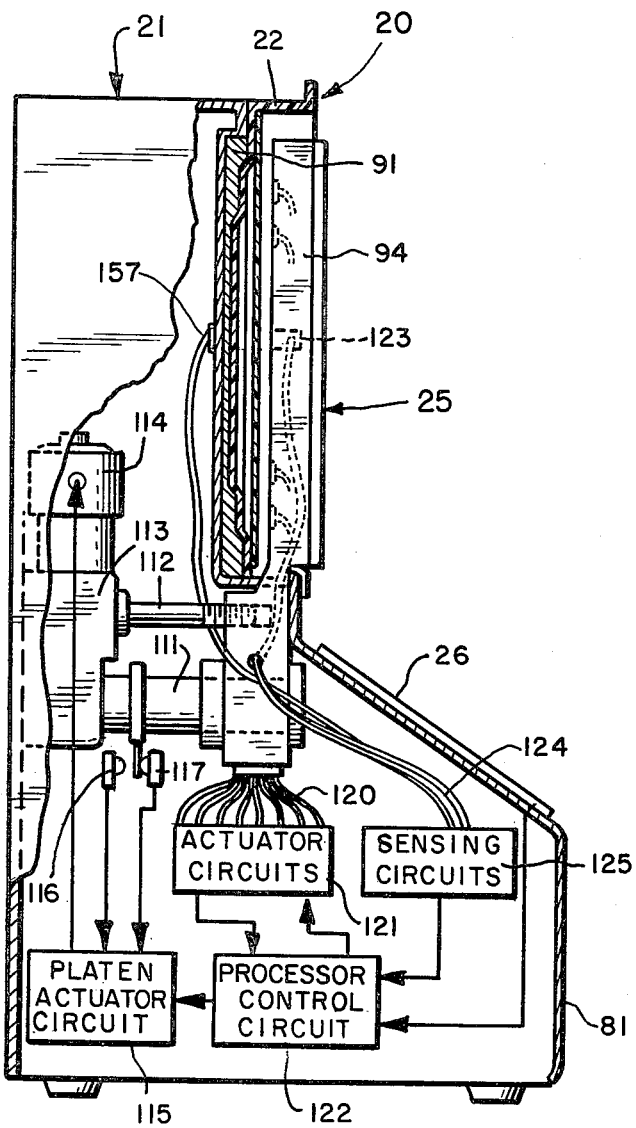
FIG. 11 is a side elevational view, partially cross-sectional and partially diagrammatic, of the processor apparatus showing the movable actuator head and actuating mechanism thereof, and the principal control circuits incorporated therein.
Figure 12:
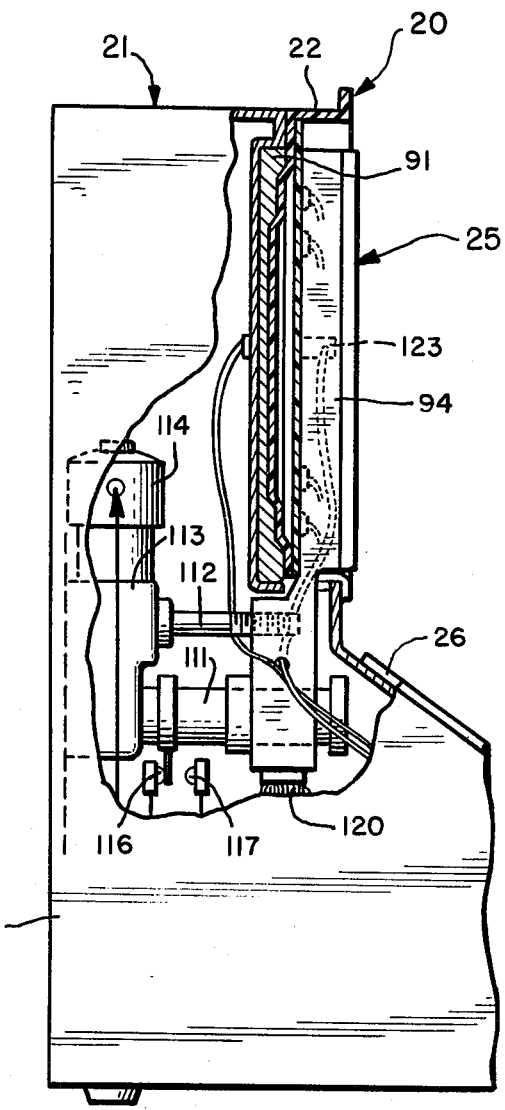
FIG. 12 is a side elevational view, similar to FIG. 11, showing the movable actuator head in a closed position engaging the processing module.

Referring to FIGS. 10–12, the actuator head 25 is mounted on a pair of parallel-spaced guide rods 110 and 111 for reciprocative movement toward and away from back plate 91. The head assembly is positioned along the guide rods by means of a jackscrew 112, drive gear assembly 113 and motor 114. Upon rotation of motor 114, the jackscrew 112 is turned and the actuator head is caused to move. An actuator head control circuit 115 functions in conjunction with limit switches 116 and 117 to limit actuator head travel between open and closed positions.

Within actuator head 25 the individual pneumatic actuator elements 100–107 are connected by respective tubing segments collectively identified as 120 to actuator circuits 121. These actuator circuits respond to electrical command signals issued by a processor control circuit 122 within processor apparatus 21 to selectively apply either a vacuum or pressure differential at the actuator ports, as required in performing the fluid processing procedure. Also, one or more sensing elements such as an ultrasonic detector 123 may be provided in the actuator head assembly to sense the occurrence of a fluid absence in the fluid circuit. This detector may be connected by conductors 124 to appropriate sensing circuits 125 within the apparatus, which provide an appropriate output signal to control circuit 122 upon the occurrence of a fluid absence. In addition, control circuit 122 may receive operator-initiated command signals from control panel 26.

In the open position of actuator head 25, as shown in FIG. 11, the housing 22 of the processing system is received with the bottom panel 36 thereof interposed between actuator plate 94 and back plate 91. Then, upon issuance of an appropriate operator-initiated signal on control panel 26, control circuits 122 condition platen actuator circuit 115 to cause motor 114 to close the actuator head. This brings the pressure actuator ports of actuator plate 94 into tight engagement with back panel 36, as shown in FIG. 12. Upon completion of the procedure, the process is reversed to enable housing 22 to be removed and the processing system to be disposed of.

Figure 13:
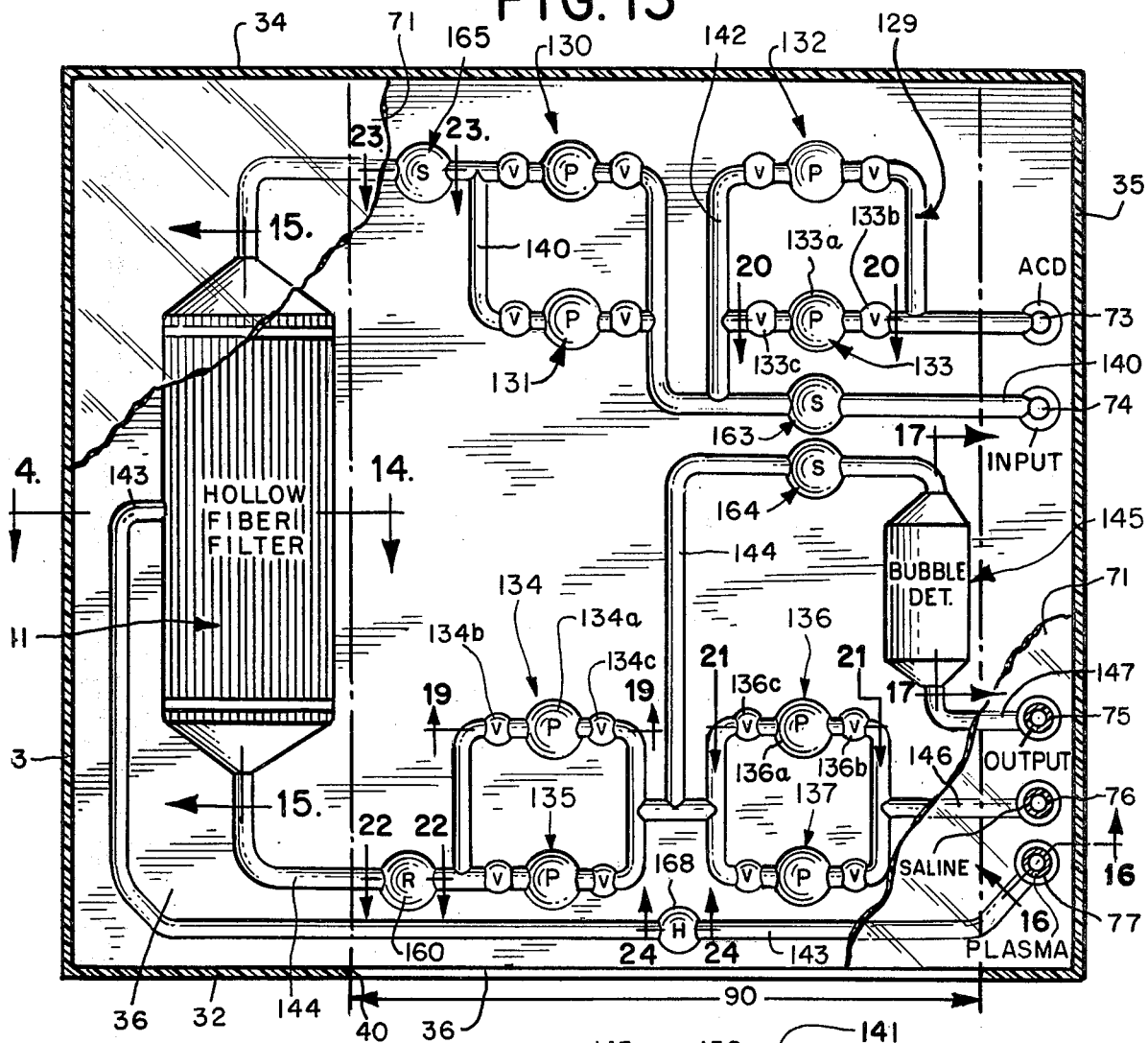
FIG. 13 is a front elevational view of the bottom panel and overlying fluid-impervious flexible sheet member of the processing module partially fragmented to show the fluid circuit formed in the underlying bottom panel.

The fluid circuit formed between the bottom panel 36 of housing 22 and the overlying fluid-impermeable sheet member 71, which is collectively identified by the number 129 in FIG. 13, includes eight preformed pump elements 130–137 for establishing flow through the fluid circuit. These pump elements, which are actuated by respective ones of actuator elements 100–108 in actuator plate 94, operate in pairs, each pair member being alternately actuated to establish a continuous flow of fluid. Pump elements 130 and 131 are paired to pump whole blood, as received from a donor through tubing segment 27 and connector 74, through a conduit segment 140 to a filter element 141. Pump elements 132 and 133 are paired to pump anticoagulant (ACD) fluid from tubing segment 56 and connector 73 through a conduit segment 142 into conduit segment 140, wherein it is combined with whole blood. Within filter element 141 plasma is separated, and separately supplied to port 77 through a conduit segment 143. Pump components 134 and 135 pump plasma-deficient whole blood from filter element 141 through a conduit segment 144 to a fluid absence detector element 145. Pump elements 136 and 137 operate to combine saline from tubing segment 60 and connector 76 through a conduit segment 146 to the plasma-deficient blood in conduit segment 144. Plasma-deficient blood from fluid absence detector element 145 is supplied through a conduit segment 147 to connector 75 and tubing segment 28 for return to the donor.

Figure 14:
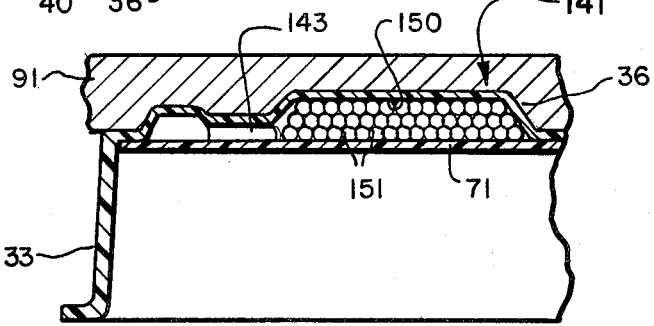
FIG. 14 is a transverse cross-sectional view of the hollow-fiber filter element of the fluid circuit taken along line 14—14 of FIG. 13.
Figure 15:
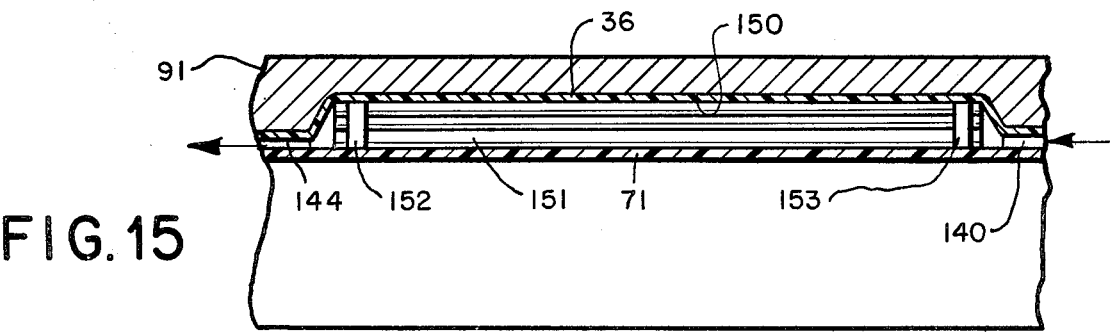
FIG. 15 is a longitudinal cross-sectional view of the filter element taken along line 15—15 of FIG. 13.

Referring to FIGS. 14 and 15, the plasma filter element 141 comprises a chamber 150 preformed within bottom panel 36 within which a plurality of hollow fiber filter elements 151 are arranged side-by-side in a longitudinal bundle to convey fluid received from conduit segment 140 to conduit segment 144. Adjacent each end of the filter bundle layers 152 and 153 of a fluid-impermeable material such as polyurethane are deposited to form liquid barriers which prevent fluid flow except through the hollow fibers of the filter. Plasma collected in the space surrounding the hollow fiber filter elements is conveyed through conduit segment 143 to connector 77 and tubing segment 46 for ultimate collection in the plasma collection container 30. While a hollow-fiber type filter membrane is shown, it will be appreciated that other forms of filter membranes, such as a flat sheet, may be provided within chamber 150 instead.

The connector element 77, which is identical in construction to connector elements 73–76, is seen in FIG. 16 to comprise a short conduit segment 154 having an outside diameter corresponding to the inside diameter of tubing segment 31. The tubing segment is forced over one end of the conduit segment, and the other end is received within a projecting flange portion 155 of the flexible sheet member 71. A bonding material is applied between the ends of the conduit segment and the sheet member and tubing segment to provide a durable fluid seal.

Referring to FIG. 17, the fluid absence detector 145 comprises a vertically-orientated chamber 156 through which plasma-deficient whole blood flows prior to being reinfused into the patient. When processing module 20 is installed in actuator 21 chamber 156 is vertically aligned, so that should a fluid absence develop, as a result of a pump malfunction, an occlusion, or any other reason, a fluid void will develop at the upper end of the chamber. A fluid detector system comprising the ultrasonic transmitter 123 on actuator plate 94 and a receiver 157 on back plate 91 sense the presence or absence of whole blood at a predetermined level 158 within chamber 156. Upon the detector sensing a fluid absence at this location, operation of the plasmapheresis processing system is terminated and an alarm is sounded, in accordance with conventional practice. The fluid detector, and its associated circuitry may be similar to that described in U.S. Pat. No. 4,341,116 of Arnold C. Bilstad and Michael Wisnienski, entitled "Liquid Absence Detector".

An alternate construction for the ultrasonic fluid absence detector is shown in FIG. 18. In this construction a combined transmitter-receiver transducer element 159 is situated on the movable actuator plate 94. The transmitter portion of the transducer introduces ultrasonic energy into chamber 156 and the detector portion of the transducer responds to reflected energy to produce an output signal indicative of the presence or absence of fluid in the chamber. In this way the detector system does not rely on the transparency of the bottom panel 36 of housing 22, thereby avoiding the possibility of the detector being rendered inoperative by tape or other material adhering to the outside surface of the bottom panel.

As shown in FIG. 13, each of the eight pump elements 130–137 in fluid circuit 129 includes a central displacement chamber (a), an upline valve stop (b), and a downline valve stop (c). As shown in FIG. 10, the eight pump actuator elements 100–107 on actuator plate 94 each include a central pumping port (a), an upline valving port (b), and a downline valving port (c), which interact with the central displacement chamber, upline valve stop, and downline valve stop of their counterpart pump elements in the fluid circuit. In addition, each of the eight pump actuator elements includes an annular hold-down port (d) which encircles the pump actuator port (a).

Figure 19A:
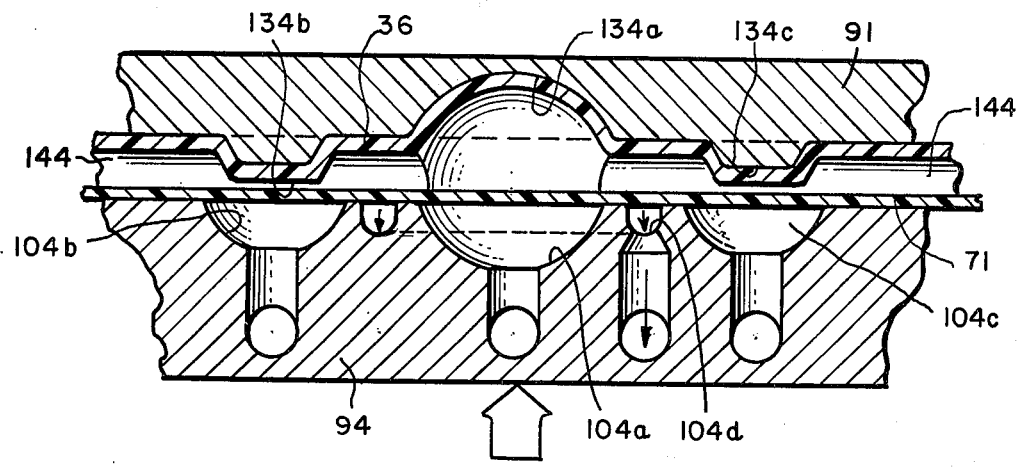
FIGS. 19A–19C are enlarged cross-sectional views of a normally closed pump element of the fluid circuit showing the element in at rest, fill and pump conditions, respectively.
Figure 19B:
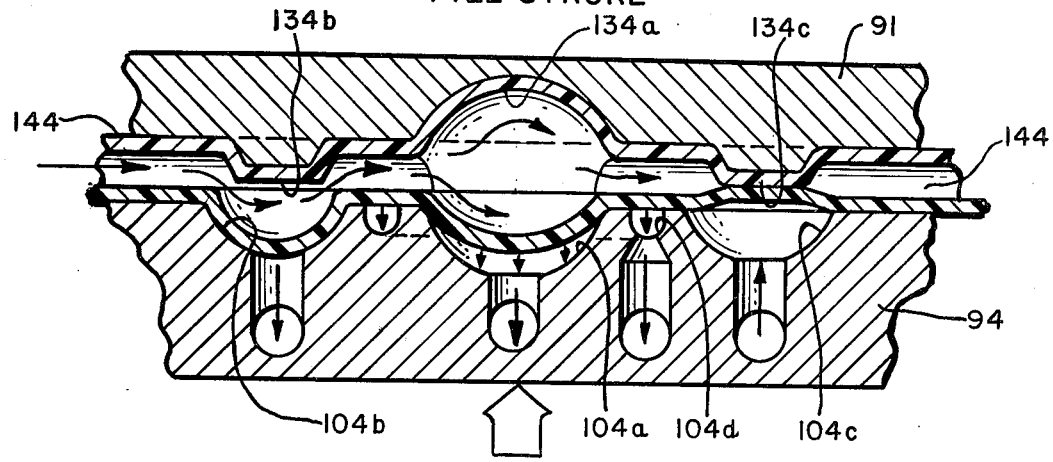
Figure 19C:
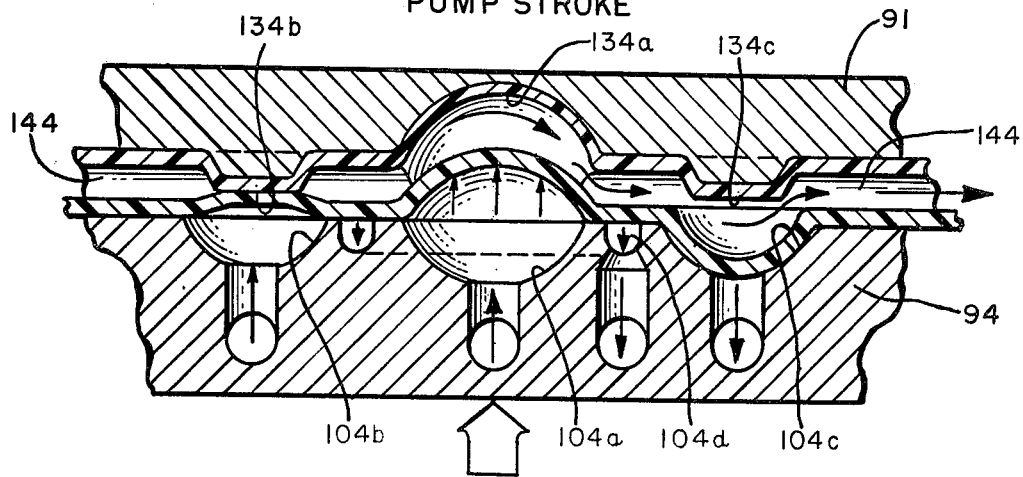

The operation of pump element 134 is illustrated in FIGS. 19A–19C. As shown in the Figures, the inlet valve consists of an actuator port 104b formed in the actuator plate 94 of the movable actuator head assembly 25, and a valve stop 134b formed in the rigid bottom panel 36 of housing 22. Similarly, the outlet valve consists of an actuator port 104c and a valve stop 134c. Each pump chamber is formed by a pump port 104a in the actuator plate and a displacement chamber 134a in the bottom panel.

At rest, as shown in FIG. 19A, processor apparatus 21 provides no vacuum at either the upline valving chamber 104b or the downline valving chamber 104c. Consequently, sheet member 71 rests in close proximity to the inlet and outlet valve seats 134b and 134c, providing a normally partially closed position.

During operation of the module, a pump fill stroke is initiated by processor apparatus 21 by drawing a vacuum in inlet valving chamber 104b to draw sheet member 71 into the valving chamber. This fully opens the inlet valve and allows fluid to flow through the valving chamber and into the displacement chamber 134a. At this time a vacuum is slowly drawn at the pumping port 104a so as to draw the sheet member 71 to the bottom (as viewed in FIG. 19B) of the displacement chamber to cause fluid to enter the chamber. At this time the downline valve is fully closed by reason of a positive pressure being applied at valving port 104c, causing sheet member 71 to be displaced against the valve stop 134c.

Upon completion of the fill stroke a pump stroke is initiated by processor apparatus 21. Inlet valving port 104b is pressurized to displace sheet member 71 against valving shoulder 134b. At the same time, a vacuum is drawn at outlet valving port 104c to draw sheet member 71 into the valving port thereby fully opening the outlet valve. A positive pressure is next slowly introduced into pumping port 104a to force sheet member 71 upwardly (as viewed in FIG. 19C) to displace fluid within the fluid displacement chamber 134a.

An alternate construction for the pump elements is shown in FIGS. 20A–20C, which depict the construction and operation of the ACD pump element 133. Instead of a normally partially closed inlet valve stop 134b provided in pump element 134, valve 133 utilizes a normally fully open valve stop 133b which is closed only during the pump stroke upon application of positive pressure to the inlet valve control port 103b, as shown in FIG. 20c. By avoiding the need to draw a vacuum in inlet valve control port 103b during rest and fill strokes valve element 133 conserves energy within the apparatus and simplifies the associated valve actuator apparatus.

The pump chamber 133a and outlet valve 133c of valve 133 are identical in construction and operation to those of valve 134. Outlet valve 133c is fully closed by positive pressure during the fill stroke, and fully opened by negative pressure and/or fluid pressure during the pump stroke. The pump element actuator ports 103a–103d are identical to those of valve 134.

Another alternate construction for the pump elements is shown in FIGS. 21A–21E, which depict the construction and operation of the bidirectional saline pump element 136. This pump element ultilizes two normally fully open valve elements 136b and 136c, which can be actuated to a fully closed position by appropriate positive pressures through pressure ports 106b and 106c respectively. As shown in FIG. 20A, at rest both valves are open and fluid can flow through the pump element.

For left-to-right flow, as illustrated in FIG. 21B and 21C, valve 136b is open during each fill stroke, and closed by positive pressure at port 106b during each pump stroke. At the same time, valve 136c is closed by pressure applied through port 106c during each fill stroke, and allowed to remain open during each pump stroke. For right-to-left flow, as illustrated in FIGS. 21D and 21E, valve 136b is closed during each fill stroke, and valve 136c is closed during each pump stroke.

Thus, valve element 136 is able to pump fluid in either direction, with a minimal pressure requirement for valve actuation. This makes the valve construction well suited for use in the saline conduit 146, where flow may take place into the system during normal replacement procedures, and out of the system during prime and purge procedures.

For optimum efficiency in separating plasma it is desirable that the transmembrane pressure (TMP) present in the hollow-fiber filter element 141 be controlled and regulated. To this end, the fluid circuit 129 includes in-line in conduit segment 144 a pressure regulator element 160. Referring to FIG. 22, this regulator comprises a valve stop 161 in the rigid bottom panel 36 and an underlying pressure port 162 in actuator plate 94. With this arrangement it is necessary that the flexible sheet member 71 be deflected downwardly into pressure port 162 and away from valve stop 161 before fluid can flow through conduit 144. Pressure regulation is provided by introducing a predetermined metering pressure in chamber 162 in opposition to deflection of sheet member 71, so that the valve opens only when the desired pressure level has been reached in conduit 144, and modulates to maintain the desired pressure once flow has been initiated. By maintaining the metering pressure constant, the desired upline pressure is maintained in conduit 144 and filter element 141.

In some applications it may be possible to avoid the need for pressure regulator element 160 by appropriately biasing the normally-closed inlet valve chambers 134b and 135b so that pump elements 134 and 135 function as pressure regulating elements. The outlet valves 134c and 135c would then remain unbiased by pneumatic pressure so as to open in response to applied fluid pressure upon the opening of inlet valves 134b and 135c.

To permit the monitoring of system operating pressures, fluid circuit 129 includes three pressure monitor elements 163–165. Pressure monitoring element 163 is located in conduit segment 140 and monitors negative pressure to detect the occurrence of a collapsed vein. Monitor 164 is located in conduit segment 144 and monitors positive pressure to detect the occurrence of an occlusion in the output circuit. Monitor 165 is located in the input conduit 140 to the filter element 141 to monitor filter inlet pressure, and hence TMP.

Referring to FIG. 23, monitor element 165, which may be identical to elements 163 and 164, is seen to comprise an in-line chamber 166 formed in conduit segment 140, and a conventional pressure transducer 167 mounted within actuator plate 94 and positioned to operatively engage the flexible sheet member as it overlies the chamber. Pressure variations in the fluid, which necessarily exist in the chamber, are reflected in changes in the electrical output signal produced by transducer 167. These signals are utilized by appropriate control circuitry in actuator apparatus 21 to provide readouts of system parameters and to control the operation of the fluid circuit.

To prevent red blood cells from being inadvertently collected in plasma collection container 30, the fluid circuit 129 includes a hemolysis detector 168 in conduit segment 143. Basically, this detector includes an in-line chamber 169 through which collected plasma is caused to flow. The presence of red blood cells in this chamber is detected by a detector 170, which may include two monchromatic light sources of different wavelengths, a light detector responsive to reflection of light from within the chamber at the two wavelengths, and circuitry responsive to the light detector for providing an alarm. The detector system may be as described in U.S. Pat. No. 4,305,659 to Arnold C. Bilstad et al., entitled "Photometric Apparatus and Method", and assigned to the present assignee.

To maintain a continuous non-pulsating flow through the fluid circuit, the paired fluid pump elements are operated in alternation. That is, when one pump component is operated in a fill stroke, its pair is operating in a pump stroke. In this way, an uninterrupted non-pulsating flow of fluid is maintained through the fluid circuit.

Specifically, elements 132 and 133 are paired and operated to introduce ACD into the main fluid conduit 140 at an operator-designated rate to prevent blood clotting. Pump elements 130 and 131 advance the whole blood obtained from the donor together with the ACD to the hollow fiber filter element 141. Within this element the whole blood is fractionated and the derived plasma component is discharged through conduit segment 143 to the plasma collection container 30.

The plasma-deficient output from filter 141 is advanced along conduit segment 144 by pump elements 134 and 135, which operate in alternation to maintain a smooth non-pulsating flow at this point. Pump elements 136 and 137 introduce saline into the main flow conduit 144 at an operator-designated rate as a plasma replacement fluid, or pump fluid and/or trapped air into saline container 44 during prime and purge procedures.

By controlling the rate at which pressure differentials are established in the pump actuator ports 100a–107a a gentle and natural pumping action is obtained which provides minimal damage to processed blood cells. The pumping rates of the individual pump elements may be set by the operator, or by automatic means within the processor apparatus responsive to measured system parameters, such as the volume and rate of plasma collection. To this end, control panel 26 (FIGS. 6 and 7) of apparatus 21 includes a selector switch 171 by which the operating speed of the anticoagulant pump element is set, a potentiometer control 172 and digital readout 173 by which the operating speed of whole blood pump elements 130, 131 and 134, 135 is controlled, and a potentiometer 174 and digital readout 175 by which the operating speed of the replacement fluid pump element 136, 137 is controlled. A plurality of push button switches 176 are provided to establish the operating mode of the apparatus, and a plurality of status-indicating lights 177 provide indications of malfunctions in the system. A digital readout 178 indicates the total volume of plasma collected, and a digital readout 179 indicates plasma collection rate. A selector switch 180 enables the replacement fluid rate to be set as a ratio of the actual plasma collection rate.

Since the displacement chambers 130a–137a of the pump elements 130–137 have a fixed and constant volume, fluid flow within the fluid circuit 129 can be controlled with great accuracy by controlling the number of pump actuations. Since each pump pulse may be treated as an aliquot, processing, proportioning and timing operations are easily accomplished in the course of the procedure.

In many procedure, such as continuous flow blood fractionation, or hemodialysis, it is desirable that the fluid being processed in fluid module 20 be maintained at a constant predetermined temperature, such as 98° F. To this end, processor apparatus 21 may, as shown in FIG. 8, include a resistance heating element 81 in back plate 91, and a resistance heating element 182 in actuator plate 94, in addition to appropriate thermal insulation for these components. These elements are powered by suitable circuitry within the processor apparatus in accordance with the temperature sensed by a temperature sensing element 183 on back plate 91 to maintain the desired temperature. Because of the minimal fluid volume in process at any one time, and the intimate contact between the fluid circuit 129 and the relatively massive actuator plate 94 and back plate 91, efficient thermal transfer is realized and fluid temperature is accurately maintained.

Alternatively, where it is desired that the fluid in process be cooled, as in cryoagulation procedures, or in the secondary treatment of plasma, cooling elements may be substituted for heating elements 181 and 182, and a secondary amount of cooling provided as sensed by temperature sensor 183.

Furthermore, while the ACD and saline containers 43 and 44 have been shown as discrete containers, it will be appreciated that with appropriate modifications to fluid circuit 129, such as the provision of valves inline with the containers, these containers as well as containers for any other fluid, stored or collected in a procedure, could be formed directly within the fluid circuit, with a construction similar to that of chamber 150 of filter element 141.

Also, while the filter element 141 has been shown as formed within the fluid circuit, it will be appreciated that if desired this element can be provided as a discrete element, apart from the fluid circuit. Connections to the element would then be made by tubing segments, as with containers 43 and 44.

Reference is made to the previously-identified copending application of the present inventors, entitled "Actuator Apparatus for a Prepackaged Fluid Processing Module Having Pump and Valve Elements Operable in Response to Applied Pressures", filed concurrently herewith, for a further explanation of processor apparatus 21.

By reason of the compact fluid circuit made possible by the integrated housing and fluid circuit, fluid connections between components of the processing system of the invention are short and direct, so that, in the case of plasmapheresis, a minimal quantity of blood is removed at any one time from the donor during processing. This minimizes trauma to the donor.

Furthermore, by reason of the pumping and valving connections to the processor being automatically established upon installation of the system housing in associated processor apparatus, set-up time is minimized to the benefit of both the operator and the donor in the plasmapheresis procedure illustrated.

While a particular embodiment of the invention has been shown and described, it will be obvious to those skilled in the art that changes and modifications may be made without departing from the invention in its broader aspects, and, therefore the aim in the appended claims is to cover all such changes and modifications as fall within the true spirit and scope of the invention.

We claim:

1. A fluid module for use in a fluid procedure, comprising:
   a housing open at one end, including a removable cover overlying said open end; and
   a relatively flexible fluid impervious sheet member within said housing forming in conjunction with said housing a fluid circuit including at least one pump element actuable in response to an applied pressure.

2. A fluid module as defined in claim 1 wherein said cover is peelably removable from said housing.

3. A fluid module as defined in claim 1 wherein said housing comprises a base panel and at least one side panel forming an open ended tray-like enclosure, and said fluid circuit is formed in conjunction with said base panel.

4. A fluid module as defined in claim 1 or 3 wherein said one pump element is responsive to a force applied to said flexible sheet member for urging fluid through said fluid circuit.

5. A fluid module as defined in claim 4 wherein said force is a pressure force.

6. A fluid module as defined in claim 1 wherein said fluid circuit is a single-use circuit, and said housing and said fluid circuit are disposable.

7. A fluid module as defined in claim 1
   wherein said housing includes a panel member formed of a relatively inflexible fluid-impermeable material and including a generally outwardly depressed portion therein; and
   wherein said relatively flexible fluid impervious sheet member overlies said panel member in fluid-sealed engagement therewith, said sheet member forming in conjunction with said depressed portion said fluid circuit which serially includes a fluid passageway and said at least one pump element responsive to said pressure applied to said flexible sheet member for controlling fluid flow in said passageway.

8. A fluid module as defined in claim 1 or 7 wherein said one pump element is actuable by a pneumatic pressure force applied to said sheet member.

9. A fluid circuit as defined in claim 8 wherein said force is applied by actuator means at a predetermined location on said sheet member and wherein said base panel comprises alignment means for maintaining said sheet member location in operative alignment with said actuator means.

10. A fluid module as defined in claim 1
    wherein said housing includes a relatively stiff fluid-impermeable base member including a raised portion thereon forming said one pump element having an inlet valve stop, an outlet valve stop, and a fluid displacement chamber being generally arranged for continuous fluid flow therethrough;
    wherein said relatively flexible fluid impervious sheet member overlies said base member in fluid-sealed arrangement therewith, and forms in conjunction with said raised portion of said base member said fluid circuit which serially includes a fluid passageway and said pump element; and
    wherein said flexible sheet member is displaceable against said inlet and outlet valve stops by pressure applied to said sheet member for closing said valve stops, and is displaceable into said fluid displacement chamber for forcing fluid along said passageway.

11. A fluid module as defined in claim 10 wherein at least one of said valve stops extends in close proximity to said flexible sheet member to form a normally partially closed valve requiring outward deflection of said flexible sheet member to fully open said valve enabling fluid passage along said passageway.

12. A fluid module as defined in claim 11 wherein both of said valve stops extend in close proximity to said flexible sheet member to form normally partially closed valves each requiring outward deflection of said flexible sheet member to fully open said valves enabling fluid passage along said passageway.

13. A fluid module as defined in claim 10 wherein at least one of said valve stops is spaced away from said flexible sheet member in the undeflected position to form a normally open valve requiring inward deflection of said flexible sheet member to close said valve.

14. A fluid module as defined in claim 13 wherein both of said valve stops are spaced away from said flexible sheet member in the undeflected position to form normally open valves requiring inward deflection of said flexible sheet member to close said valves.

15. A modular fluid processing system for use in a fluid procedure, comprising:
    a housing have a base panel and at least one side panel;
    at least one system element contained within said housing for use in conjunction with the procedure; and
    a fluid-impermeable sheet member within said housing overlying said base panel, and forming in conjunction with said base panel a fluid circuit in fluid communication with said component.

16. A fluid module as defined in claim 15 wherein said cover is open at at least one end, and includes a removable cover overlying said open end.

17. A fluid module as defined in claim 16 wherein said cover is peelably removable from said housing.

18. A fluid module as defined in claim 15 wherein said sheet member is relatively flexible, and said fluid circuit includes a circuit element responsive to an applied force for forcing fluid through said circuit.

19. A fluid module as defined in claim 18 wherein said fluid circuit includes a filter element.

20. A fluid module as defined in claim 18 wherein said circuit element is responsive to displacement of a portion of said overlying fluid-impermeable sheet member in response to an applied pneumatic pressure differential.

21. A fluid module as defined in claim 20 wherein said circuit element comprises a pump element for urging fluid through said circuit.

22. A fluid module as defined in claim 11 wherein said base panel is relatively stiff and includes an outwardly deformed portion forming in conjunction with said overlying sheet member said fluid circuit, and wherein said overlying sheet member is relatively flexible, and wherein said fluid circuit includes a circuit element actuable by a force applied to said sheet member.

23. A fluid module as defined in claim 22 wherein said applied force comprises a pressure.

24. A fluid module as defined in claim 23 wherein said pressure differential is applied by actuator apparatus external to said housing, and said side panel includes at least one aperture facilitating pressure communication between said actuator apparatus and said flexible sheet member.

25. A fluid module for fractionating a desired fluid component from a whole fluid, said module comprising, in combination
   a housing having a base panel and at least one side panel;
   a filter element for separating the desired component from the whole component; and
   a fluid-impervious sheet member within said housing overlying said bottom panel, said bottom panel including a depressed portion forming in conjunction with said overlying sheet member a fluid circuit serially including said filter element.

26. A fluid module as defined in claim 25 wherein said housing is open at one end and includes a removable cover enclosing said housing.

27. A fluid module as defined in claim 26 wherein said cover is peelably removable from said housing.

28. A fluid module as defined in claim 25 wherein said base panel is outwardly deformed to form in conjunction with said overlying sheet member a filter chamber, and wherein said filter element is disposed within said chamber.

29. A fluid module as defined in claim 28 wherein said filter element comprises a hollow-fiber filter element.

30. A fluid module as defined in claim 25, wherein said housing contains a container for fluid involved in the fractionation procedure, and said fluid circuit is in fluid communication with said container.

31. A fluid module as defined in claim 25 wherein said housing and said sheet member are disposable members formed of a plastic material.

32. A modular fluid system for performing a fluid procedure, comprising:
   a housing open at one end and including a base panel and at least one side panel formed of a relatively inflexible fluid-impermeable plastic material;
   a system component contained within said housing for use in conjunction with said fluid procedure;
   a relatively flexible fluid-impermeable sheet member overlying said base panel, said base panel including an outwardly depressed portion thereon forming in conjunction with said sheet member a fluid-sealed fluid circuit including a circuit element actuable by force applied to said sheet member; and
   removable cover means overlying the open end of said housing.

33. A fluid module as defined in claim 32 wherein said circuit element comprises a pump element actuable by pressure applied to said flexible sheet member.

34. A fluid module as defined in claim 33 wherein said side panel includes an access aperture to facilitate application of pressure to said sheet member.

35. A fluid module as defined in claim 32 wherein said system container is connected in fluid communication with said fluid circuit, and removable from said housing through said open end.

36. A fluid module for use in a fluid procedure comprising
   a housing comprising a base panel and at least one side panel forming an open ended tray-like enclosure, and
   a relatively flexible fluid impervious sheet member within said housing forming in conjunction with said base panel a fluid circuit including at least one pump element actuable in response to an applied pressure.

37. A fluid module as defined in claim 36 and further including a cover over said open end for closing said housing.

38. A fluid module as defined in claim 37 wherein said cover is peelably removable from said housing.

39. A fluid module as defined in claim 36 wherein said one pump element is responsive to a force applied to said flexible sheet member for urging fluid through said fluid circuit.

40. A fluid module as defined in claim 36
   wherein said base panel is formed of a relatively inflexible fluid-impermeable material and includes a generally outwardly depressed portion therein; and
   wherein said relatively flexible fluid impervious sheet member overlies said base panel in fluid-sealed engagement therewith, said sheet member forming in conjunction with said depressed portion said fluid circuit which serially includes a fluid passageway and said at least one pump element responsive to said pressure applied to said flexible sheet member for controlling fluid flow in said passageway.

41. A fluid module as defined in claim 39 or 40
   wherein said one pump element is actuable by a pneumatic pressure force applied to said sheet member.

42. A fluid module as defined in claim 36
   wherein said base panel includes a raised portion thereon forming said one pump element having an inlet valve stop, an outlet valve stop, and a fluid displacement chamber being generally arranged for continuous fluid flow therethrough;
   wherein said relatively flexible fluid impervious sheet member overlies said base panel in fluid-sealed arrangement therewith, and forms in conjunction with said depressed portion of said base panel said fluid circuit which serially includes a fluid passageway and said pump element; and
   wherein said flexible sheet member is displaceable against said inlet and outlet valve stops by pressure applied to said sheet member for closing said valve stops, and is displaceable into said fluid displacement chamber for forcing fluid along said passageway.

43. A fluid module as defined in claim 42
   wherein at least one of said valve stops extends in close proximity to said flexible sheet member to form a normally partially closed valve requiring outward deflection of said flexible sheet member to fully open said valve enabling fluid passage along said passageway.

44. A fluid module as defined in claim 43
   wherein both of said valve stops extend in close proximity to said flexible sheet member to form normally partially closed valves each requiring outward deflection of said flexible sheet member to fully open said valves enabling fluid passage along said passageway.

45. A fluid module as defined in claim 42 wherein at least one of said valve stops is spaced away from said flexible sheet member in the undeflected position to form a normally open valve requiring inward deflection of said flexible sheet member to close said valve.

46. A fluid module as defined in claim 45 wherein both of said valve stops are spaced away from said flexible sheet member in the undeflected position to form normally open valves requiring inward deflection of said flexible sheet member to close said valves.

* * * * *